US011109975B2

(12) United States Patent
Estes et al.

(10) Patent No.: US 11,109,975 B2
(45) Date of Patent: Sep. 7, 2021

(54) ARTICULAR CARTILAGE REPAIR

(71) Applicant: Cytex Therapeutics, Inc., Durham, NC (US)

(72) Inventors: Bradley T. Estes, Durham, NC (US); Franklin Thomas Moutos, Raleigh, NC (US); Farshid Guilak, Durham, NC (US)

(73) Assignee: Cytex Therapeutics, Inc., Durham, NC (US)

( * ) Notice: Subject to any disclaimer, the term of this patent is extended or adjusted under 35 U.S.C. 154(b) by 0 days.

(21) Appl. No.: 14/862,536

(22) Filed: Sep. 23, 2015

(65) Prior Publication Data
US 2016/0081807 A1 Mar. 24, 2016

Related U.S. Application Data

(60) Provisional application No. 62/053,883, filed on Sep. 23, 2014.

(51) Int. Cl.
*A61F 2/30* (2006.01)
*A61L 27/18* (2006.01)
(Continued)

(52) U.S. Cl.
CPC ...... *A61F 2/30756* (2013.01); *A61L 27/3852* (2013.01); *A61F 2002/2817* (2013.01);
(Continued)

(58) Field of Classification Search
CPC .... A61K 2300/00; A61K 35/32; A61K 38/18; A61K 38/1841; A61K 47/36; A61K 9/00; A61K 9/1682; A61K 9/70; A61L 27/54; A61L 2430/02; A61L 27/56; A61L 2430/10; A61L 2430/34; A61L 27/50; A61L 27/3817; A61L 27/446; A61L 27/3608; A61L 31/16; A61L 2300/412; A61L 2400/18; A61L 2430/38; A61L 27/365; A61L 27/3654; A61L 27/52; A61L 2430/24; A61L 2400/08; A61F 2002/2835;
(Continued)

(56) References Cited

U.S. PATENT DOCUMENTS

2003/0003135 A1\* 1/2003 Leung ................ A61K 9/0009
424/443
2005/0008675 A1 1/2005 Bhatia et al.
(Continued)

FOREIGN PATENT DOCUMENTS

WO 2014055480 A1 4/2014

OTHER PUBLICATIONS

International Search Report corresponding to International Appl. No. PCT/US2015/051695, dated Dec. 15, 2015 (8 pages).
(Continued)

*Primary Examiner* — Ann Schillinger
(74) *Attorney, Agent, or Firm* — Maginot, Moore & Beck, LLP

(57) ABSTRACT

A scaffold is provided which facilitates integration of both bone and cartilage at an osteochondral lesion, thereby acting as a tissue engineered interface or tissue engineered junction between the two different tissues. The method and systems for engineering this interface may be acellular or may be loaded with cells prior to use.

18 Claims, 4 Drawing Sheets

(51) Int. Cl.
  *A61L 27/30* (2006.01)
  *A61L 27/38* (2006.01)
  *A61F 2/28* (2006.01)

(52) U.S. Cl.
  CPC ............ *A61F 2002/3092* (2013.01); *A61F 2002/3093* (2013.01); *A61F 2002/30766* (2013.01); *A61F 2002/30838* (2013.01); *A61F 2002/30971* (2013.01); *A61L 2430/34* (2013.01)

(58) Field of Classification Search
  CPC ............ A61F 2/30756; A61F 2/28; A61F 2002/30766; A61F 2002/30062; A61F 2002/30985; A61F 2/30942; A61F 2/3872; A61F 2002/3093; A61F 2210/0004; A61F 2002/2839; A61F 2002/3092; A61F 2310/00359; A61F 2/30767; A61F 2002/0068; A61F 2002/30011; A61F 2002/30028; A61F 2002/3006
  See application file for complete search history.

(56) References Cited

U.S. PATENT DOCUMENTS

| | | | |
|---|---|---|---|
| 2005/0043814 A1 | 2/2005 | Kusanagi et al. | |
| 2005/0118236 A1* | 6/2005 | Qiu | A61L 27/10 424/443 |
| 2005/0222591 A1* | 10/2005 | Gingras | A61F 2/0063 606/151 |
| 2007/0041952 A1 | 2/2007 | Guilak | |
| 2007/0255422 A1* | 11/2007 | Wei | A61F 2/28 623/23.51 |
| 2009/0196901 A1* | 8/2009 | Guilak | A61K 35/32 424/423 |
| 2011/0206828 A1 | 8/2011 | Liu et al. | |
| 2015/0148823 A1* | 5/2015 | Mortarino | A61F 2/0063 606/151 |
| 2015/0238318 A1* | 8/2015 | McCullen | A61F 2/3872 623/14.12 |

OTHER PUBLICATIONS

Aichroth, P.M., et al. "A Prospective Review of Arthroscopic Debridement for Degenerative Joint Disease of the Knee," International Orthopaedics (SICOT) (1991) 15: 351-355.
Aubin, P.P., MD, et al. "Long-Term Followup of Fresh Femoral Osteochondral Allograft for Posttraumitc Knee Defects," Clinical Orthopaedics and Related Research No. 391S, pp. S318-S327.
Bedi, Asheesh, MD, et al., "Current Concepts Review Management of Articular Cartilage Defects of the Knee," The Journal of Bone and Joint Surgery, Inc., 2010; 92; pp. 994-1009.
Buckwalter, Joseph A., et al., "Perspectives on Chondrocyte Mechanobiology and Osteoarthritis," Bioreology 43 (2006) pp. 603-609.
Baumgaertner, Michael R., M.D., et al., "Arthroscopic Debridement of the Arthritic Knee," Section of Orthopaedics, Veterans Administration Medical Center, Sep. 27, 1988.
Chuan Chen, Wei, et al., "Evaluating Osteochondral Defect Repair Potential of Autologous Rabbit Bone Marrow Cells on Type II Collagen Scaffold," Cytotechnology (2011) 63: pp. 13-23.
Denoncourt, PM, et al., "Arthroscopy Update #1. Treatment of Osteochondrosis Dissecans of the Knee by Arthroscopic Curettage, Follow-up Study," Orthop Rev., Oct. 1986; (10): 652-7.
Emmerson, Bryan C., et al., "Fresh Osteochondral Allografting in the Treatment of Osteochondritis Dissecans of the Femoral Condyle," The American Journal of Sports Medicine, vol. 35, No. 6 DOI.
Farr, Jack, MD, et al. "Clinical Cartilage Restoration," Clin Orthop Relat Res (2011) 469: pp. 2696-2705.
Friedman, Marc J., et al., "Preliminary Results with Abrasion Arthroplasty in the Osteoarthritic Knee," Southern California Sports Medicine and Orthopedic Medical Group, Center for Disorders of the Knee, Van Nuys, CA.
Ghazavi, M.T., et al., "Fresh Osteochondral Allografts for Post-Traumatic Osteochondral Defects of the Knee," The Journal of Bone and Joint Surgery, 1997; 79-B, pp. 1008-1013.
Gille, J., et al., "Mid-Term Results of Autologous Matrix-Induced Chondrogenesis for Treatment of Focal Cartilage Defects in the Knee,"Knee Surg Sports Traumatol Arthrosc (2010) 18: pp. 1456-1464.
Hjelle, Karin, M.D., et al., "Articular Cartilage Defects in 1,000 Knee Arthroscopies," Arthroscopy: The Journal of Arthroscopic and Related Surgery, vol. 18, No. 7 Sep. 2002: pp. 730-734.
Johnson, Lanny L., MD, "Clinical Methods of Cartilage Repair," Clinical Orthopaedics and Related Research, No. 391S, pp. S306-S317.
Kalson, N.S., et al., "Current Strategies for Knee Cartilage Repair," The International Journal of Clinical Practice, Sep. 2010, 64, 10, pp. 1444-1452.
Kish, Gary, MD, et al., "Osteochondral Mosaicplasty for the Treatment of Focal Chondral and Osteochondral Lesions of the Knee and Talus in the Athlete," Clinics in Sports Medicine, vol. 18, No. 1, Jan. 1999.
McNickle, Allison G., et al., "Overview of Existing Cartilage Repair Technology," Sports Med Arthrosc Rev, vol. 16, No. 4, Dec. 2008.
Nehrer, Stefan, MD, "Histologic Analysis of Tissue After Failed Cartilage Repair Procedures," Clinical Orthopaedics and Related Research, No. 365, pp. 149-162.
Nettles, Dana L., et al. "Photocrosslinkable Hyaluronan as a Scaffold for Articular Cartilage Repair," Annals of Biomedical Engineering, vol. 32, No. 3, Mar. 2004, pp. 391-397.
Patrascu, J.M., et al., "Repair of a Post-Traumatic Cartilage Defect with a Cell-Free Polymer-Based Cartilage Implant," The Journal of Bone and Joint Surgery, 2010; 92-B: pp. 1160-1163.
Shapiro, Frederic, M.D., "Cell Origin and Differentiation in the Repair of Full-Thickness Defects of Articular Cartilage," The Journal of Bone and Joint Surgery, 1993.
Siclari, Alberto, MD, et al., "A Cell-Free Scaffold-Based Cartilage Repair Provides Improved Function Hyaline-Like Repair at One Year," Clin Orthop Relat Res (2012) 470: pp. 910-919.
Steadman, J. Richard, et al., "Microfracture: Surgical Technique and Rehabilitation to Treat Condral Defects," Clinical Orthopaedics and Related Research, No. 319S, pp. S362-S369.
Steadman, J. Richard, et al., "Outcomes of Microfracture for Traumatic Chondral Defects of the Knee: Average 11-Year Follow-Up," The Journal of Arthroscopic and Related Surgery, vol. 19, No. 5 May-Jun. 2003, pp. 477-484.
Tetteh, Elizabeth S., MD, et al., "Basic Science and Surgical Treatment Options for Articular Cartilage Injuries of the Knee," Journal of Orthopaedic & Sports Physical Therapy, vol. 42, No. 3, Mar. 2012.
Tew, Simon R., et al., "The Reactions of Articular Cartilage to Experimental Wounding," Arthritis & Rheumatism, vol. 43, No. 1, Jan. 2000, pp. 215-225.
Hardaker, William T., et al., "An Algorithm for Arthroscopy in the Over-50 Age Group," The American Journal of Sports Medicine, vol. 20, No. 2, 1992.
Zantop, Thore, M.D, and Petersen, Wolf, M.D. Ph.D., "Arthroscopic Implantation of a Matrix to Cover Large Chondral Defect During Microfracture," The Journal of Arthroscopic and Related Surgery, vol. 25, No. 11 Nov. 2009: pp. 1354-1360.
European Search Report in corresponding case EP15843421, dated Jan. 22, 2019.

\* cited by examiner

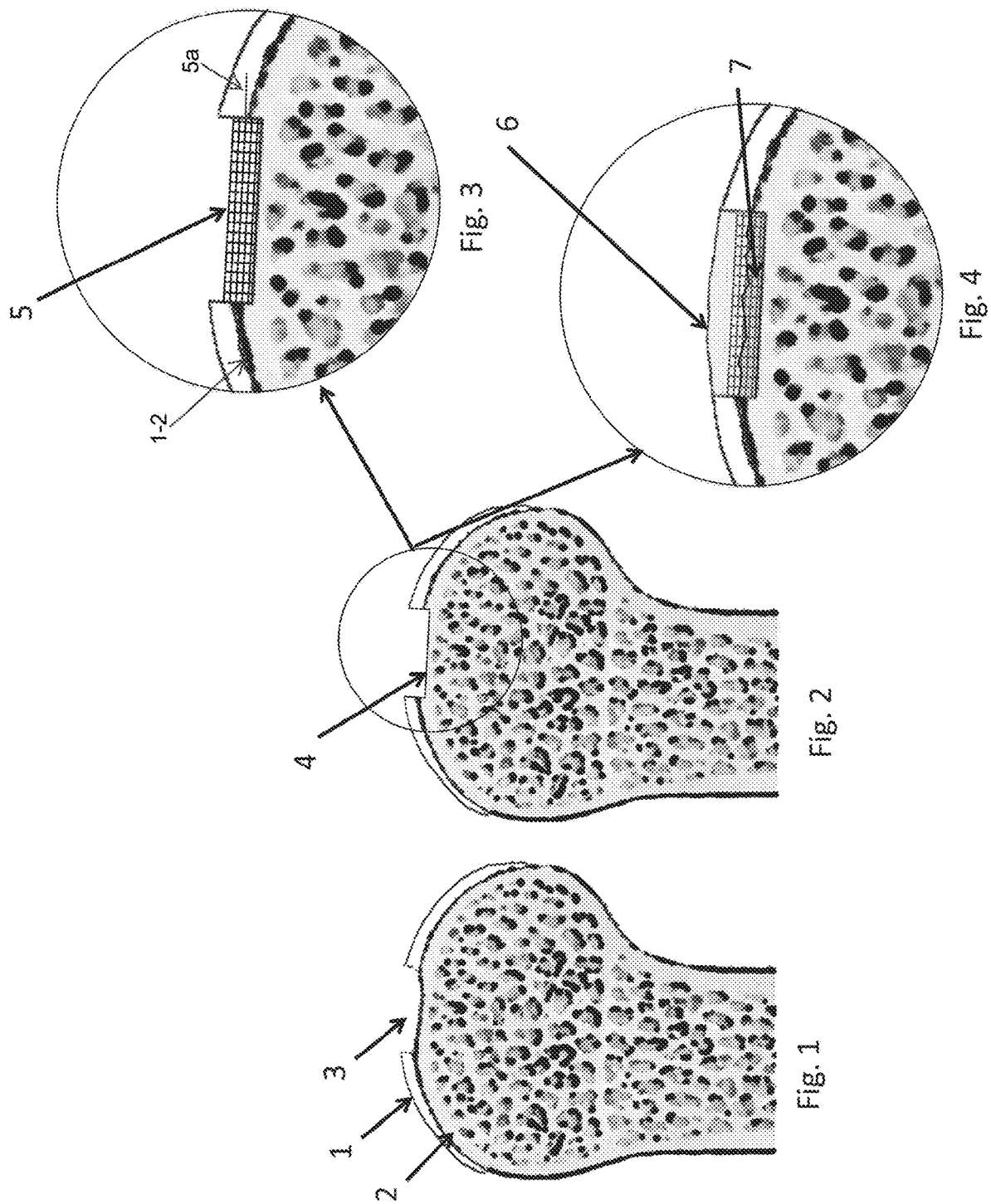

ARTICULAR CARTILAGE REPAIR

REFERENCE TO RELATED APPLICATION AND PRIORITY CLAIM

This application is a utility filing of and claims priority to provisional application No. 62/053,883, filed on Sep. 23, 2014, the entire disclosure of which is incorporated herein by reference.

BACKGROUND

Damage to articular cartilage is a significant clinical problem with over 50% of orthopaedic injuries involving the cartilage in articular joints, and recent statistics suggest that cartilage lesions are found in 61% of knee arthroscopies, with 19% of these being focal or osteochondral in nature (1). [The parenthetic numerals refer to the references listed at the end of the specification]. Cartilage injury often progresses to osteoarthritis (OA), highlighting the need for successful treatments at the primary intervention (2). Because articular cartilage has little intrinsic ability for self-healing, cartilage injury results in a burgeoning economic burden for both primary and follow-up treatment costs, estimated at more than 40 billion dollars annually in the U.S. alone (3). Unfortunately, surgeons have few available options for the repair of acute cartilage injury. Current treatment options include joint lavage, tissue debridement, abrasion arthroplasty, microfracture of the subchondral bone, or the transplantation of autologous or allogeneic osteochondral grafts (4-15). While these procedures have yielded promising clinical results, many of these approaches can lead to the formation of fibrous tissue, apoptosis, and further cartilage degeneration (16-18). This has led to a flurry of research and development activity aimed at gaining improved cartilage repair strategies that have resulted in more than twenty cartilage tissue engineering products in recent years (19). However, these products focus largely on biomaterials that improve upon methods to trap cells within a defect or on creating bilayer osteochondral implants to recreate the bilayer structure of osteochondral tissue (e.g., cartilage repair device (β-TCP/PLA/collagen scaffold-Kensey Nash) and TruFit CB® plug (biphasic polylactide coglycolide, calcium sulfate, and polyglycolide fibers of Smith and Nephew, Inc., London, UK)), but they do not recapitulate the mechanical properties of the native tissues. Other synthetic materials have also been extensively studied for cartilage tissue engineering (e.g., α-hydroxy esters (e.g., polyglycolic acid and polylactic acid), peptide-modified polymers, collagen, hyaluronic acid, and chitosan, along with macroporous hydrogels of agarose and alginate), but these materials generally lack appropriate functional mechanical properties and have suffered from the inability to maintain congruity and appropriate geometry as cells remodel the matrix (e.g., (20, 21)).

Of the cartilage pathology treatments currently available in the clinic, microfracture surgery remains the most widely used surgical procedure for treatment of articular cartilage defects (22). This procedure can be performed arthroscopically and is relatively straightforward, which make it an attractive option for both the patient and the surgeon. Although mesenchymal stem cells (MSCs) are released by the fracturing techniques used, these cells tend to differentiate into fibrochondrocytes and support the generation of reparative tissue containing a high concentration of type I collagen (23). As a result, this neotissue can range from a predominantly fibrocartilaginous composition to a mix of hyaline-like and fibrocartilage, and is therefore biomechanically inferior to the surrounding healthy cartilage, compromising its ability to withstand the high compressive and shear loading associated with normal joint function (24, 25). Moreover, the stable formation of repair tissue that maximally fills the defect area has been shown to be strongly correlated with the success of microfracture (24). Therefore, efforts have been made to enhance microfracture by implanting an acellular scaffold in the defect site at the time of surgery. However, in most of the reported cases, the perforated and bleeding subchondral bone was covered by a nonwoven mesh of polyglycolic acid (PGA) fibers (26-28), whose quick resorption (~50% in 1 week) precludes its ability to provide load-bearing mechanical properties in mid- or long-term, as demonstrated by a decline in functional scores beyond 3 years (29) in follow up MRI. This suggests that an implantable scaffold with the ability to more closely recreate the functional properties of articular cartilage for a longer period of time could improve the long-term outcomes of nearly all microfracture procedures, particularly for large defects.

Guilak et al. disclose a 3D woven scaffold for cartilage tissue resurfacing in U.S. Pat. No. 8,691,542; however, in this patent the inventors use the 3D woven scaffold to resurface a number of defects in the cartilage surface. The 3D scaffold in the '542 patent is used to replace the articular cartilage surface and not to integrate the bone and cartilage tissue layers as is disclosed in the current application. Others have disclosed the use of multiphasic materials for the use of osteochondral tissue engineering. U.S. Pat. Nos. 7,776,100 and 7,963,997 disclose a cartilage region comprising a polyelectrolytic complex joined with a subchondral region with a hydrophobic barrier between the regions, wherein the polyelectrolytic complex transforms to a hydrogel. U.S. Pat. No. 6,319,712 discloses a biohybrid articular surface replacement in the form of a three-dimensional, porous carrier for cell growth and tissue development with a separate agent for aiding in osseous integration.

U.S. Pat. No. 6,306,169 discloses a biomechanical implant that is composed of two matrix components, the first of which is composed of a collagen and the second component a hydrated alginate for use in damaged cartilage tissue. U.S. Pat. No. 5,607,474 discloses a carrier for supporting replenished tissue growing in a diseased or damage system of a region of tissue having different mechanical properties. In this patent, the inventors disclose two porous layers that are amenable to tissue growth of the two different layers of tissue with corresponding mechanical properties of the two disparate tissue layers. U.S. Pat. No. 7,217,294 discloses the use of a two or three dimensional biodegradable scaffold implanted in the osteochondral lesion below one or more layers of sealants, wherein the sealants separate the layers of bone and cartilage.

U.S. Pat. No. 5,842,477 discloses the implantation of a three-dimensional scaffold structure in combination with periosteal or perichondrial tissue for the purposes of cartilage repair. U.S. Pat. No. 9,072,815 discloses a multilayered collagen scaffold suitable for osteochondral tissue repair comprising a first layer of type I collagen and hyaluronic acid, a second layer comprising a mixture of type I and II collagen and hyaluronic acid and a third layer of type I and type II collagen and another polymer or biologic (e.g., glycosaminoglycan).

While the aforementioned patents disclose methods and implants for treating cartilage defects, they all rely on at least two different components in a layered approach (biphasic or triphasic) to repair the osteochondral lesion (i.e., bone and cartilage) and restore congruity at the joint surface. The implants and methods disclosed herein differ from these prior techniques in that the presently disclosed methods and disclosed implants do not replace either tissue (bone and cartilage) but rather provide a means to repair the interface between the two tissues and thus anchor the de novo tissue generated within and eventually extending out of the interfacial implant.

U.S. Pat. No. 8,685,107 discloses a double-structured tissue implant comprising a primary scaffold with a plurality of pores and a secondary cross-linked collagenous scaffold within said pore structure for the repair of cartilage defects. This is a single-phase (i.e., one structure consisting of the combination of two materials) composite material for the purposes of cartilage repair and thus seeks the restoration of the cartilage layer upon implantation. U.S. Pat. Nos. 8,192,759, 8,444,968, 8,512,730, and 8,580,289, in a similar manner to the '107 patent discussed above, disclose a single phase implant for osteochondral (as well as using the same material for other tissues) repair with a matrix comprising a polyester polymer entangled with a polysaccharide polymer.

U.S. Pat. No. 5,736,372 discloses cells mixed with a biocompatible matrix consisting of polymer fibers, incubated in vitro, and then implanted into the cartilage defect to ultimately form a cartilaginous structure in vitro. This is also a single-phase mixture for articular cartilage repair, does not contain an ordered, woven matrix and does not address the integration of bone and cartilage as is achieved by the implants and methods of the present disclosure.

U.S. Pat. No. 8,226,715 discloses a plurality of 3D woven bioresorbable fibers for the purposes of tendon and ligament reconstruction. The woven structure of the '715 Patent is one method for anchoring the tendon/ligament repair device into the bone, and thus differs from the implants and methods of the present disclosure in that it is not intended to provide a region for incorporation of the two tissues of bone and ligament.

Accordingly, the implants and methods of the present disclosure respond to the deficiencies of current clinical treatment options for treating osteochondral pathology. By effectively providing and thus repairing the interface between the two tissues, the implants and methods described herein use 3D woven warp interlock fabrics to manufacture scaffolds, which can be firmly integrated into bone while also serving as a substrate for synthesis of a functional cartilage layer. In this way, the implants and methods of the present disclosure result in a complete filling of the defect with a biosynthetic implant capable of functioning within the harsh joint environment, thereby overcoming the insufficiencies of current clinical osteochondral repair strategies.

SUMMARY

The present disclosure is directed at methods and systems for articular cartilage repair for the purpose of restoring the native structure and function to tissues that have been lost or degenerated due to osteochondral lesions. The present disclosure introduces the use of a porous scaffold for the purposes of directing repair of the interface between bone and cartilage. In one aspect of the present disclosure, a bone bed is prepared with complementary structure to that of the porous scaffold followed by placement of the scaffold in apposition with the prepared bed. Adequate preparation often results in bone marrow exuding through the bone and therefore into and around the porous scaffold once placed in the prepared bed. The porous scaffold acts as a common anchor point between the two disparate tissues and thus facilitates the synthesis of bone on one side and into the scaffold, while supporting the ingrowth and maturation of cartilaginous tissue on and into the other side of the implant. Another feature is that the functional properties of the interfacial implant have been designed to mimic many of the native properties of the cartilage layer.

More specifically, the implants and methods of the present disclosure make use of warp interlock weaving to customize regions of the scaffold for cartilage and bone-like functional properties along with ideal properties for biological incorporation in the different regions or zones of the implant. The 3D woven implant consists of a series of in-plane warp fibers (x-fibers) filled with weft fibers (y-fibers) between warp layers and then bound together with z-binder yarns. One of the advantages gained with 3D weaving over traditional weaving methods is the ability to manufacture near net shape implants by molding after the weaving process, which effectively allows conformity to the specific lesion being treated. The structure also offers excellent delamination resistance, high impact damage tolerance, and robust compressive properties. Lastly, due to the inherent control of the fibers used in weaving the material, the implant porosity and strength (as a function of number of binding warp yarns, number of stuffer warp yarns, number of surface weave warp yarns, number of weft yarns layers, weave diagrams per layer, warping formulae, weft insertion formulae, density of binding warp yarns, density of stuffer warp yarns, density of surface weave warp yarns, density of weft yarns per layer, material choice, fiber diameter, and fiber type) is tailored to that of the bone and cartilage tissues.

BRIEF DESCRIPTION OF THE DRAWINGS

FIG. 1 is a cross-section (sagittal) 2D view of a long bone showing an osteochondral defect.

FIG. 2 is a cross-section (sagittal) 2D view of a long bone after preparation of the defect site.

FIG. 3 is a magnified image of FIG. 2 showing interfacial implant in the defect.

FIG. 4 is a magnified image of FIG. 2 illustrating how the interfacial implant consolidates the repair from both sides of the implant.

DETAILED DESCRIPTION

Figure 7:
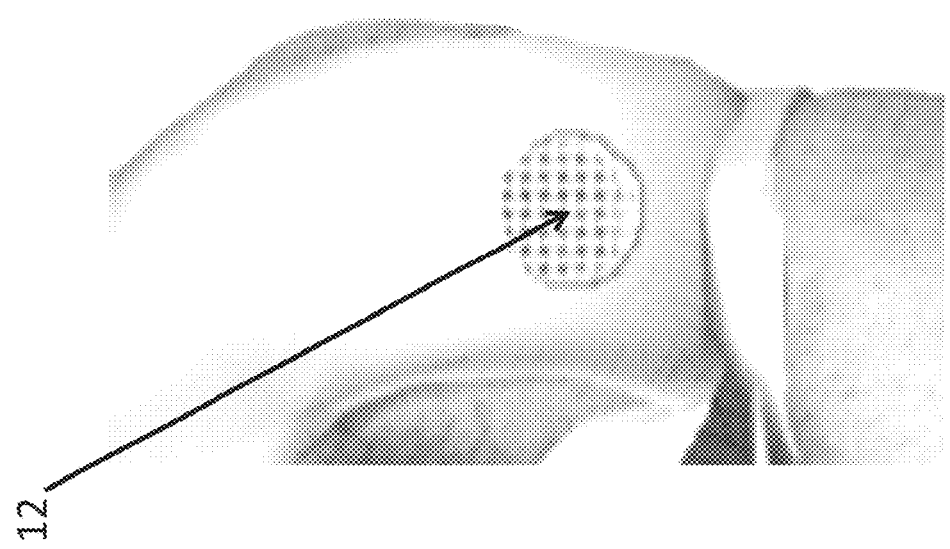
FIG. 7 is a front perspective view after the prepared defect has been filled with the interfacial implant.

For the purposes of promoting an understanding of the principles of the invention, reference will now be made to the embodiments described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The interfacial implant of the present disclosure comprises a three-dimensional fiber scaffold tailored to match one or more of the principal native tissue properties, including, but not limited to: compressive modulus, tensile modulus, inhomogeneity, anisotropy, Poisson's ratio, non-linearity, and viscoelasticity. The interfacial implant comprises at least three systems of fibers defining an upper, middle, and lower layer. The layers in combination recreate many of the native properties of the tissue and facilitate the anchorage of the cartilage and bone during healing of the defect. It follows that the tissue grows in and throughout the interfacial implant.

In one aspect, the interfacial implant is constructed using three-dimensional (3D) warp interlock structures as described in: "General definition of 3D warp interlock fabric architecture" (Boussu F, Cristian I, Nauman S, Composites Part B: Engineering. 2015; 81:171-88. doi: http://dx.doi.org/10.1016/j.compositesb.2015.07.013); "Fibre damage in the manufacture of advanced three-dimensional woven composites" (Rudov-Clark S, Mouritz A P, Lee L, Bannister M K, Composites Part A: Applied Science and Manufacturing. 2003; 34(10):963-70. doi: http://dx.doi.org/10.1016/S1359-835X(03)00213-6); and "Behavior of 3D orthogonal woven CFRP composites. Part I. Experimental investigation" (Tan P, Tong L, Steven G P, Ishikawa T., Composites Part A: Applied Science and Manufacturing. 2000; 31(3):259-71. doi: http://dx.doi.org/10.1016/S1359-835X(99)00070-6), the entire disclosure of each reference of which is incorporated herein by reference. The interfacial implant may also be fabricated by knitting, braiding, or non-woven processes or combinations thereof, or in combination with the warp interlock fabrics described above.

The interfacial implant has controlled porosity with pores on the order of 50-1000 μm to allow through growth and consolidation of the tissue in the interfacial implant. The interfacial implant comprises fibers made from biocompatible materials, which may be multifilament fibers, monofilament fibers, filaments that have variable or irregular cross-section along its length, hollow fibers, or any combination thereof. The fibers are preferably on the order of 25-300 μm in thickness or diameter. The biocompatible fibers are comprised of bioresorbable biomaterials, non-bioresorbable biomaterials, or combinations thereof. Representative non-bioresorbable materials include but are not limited to polypropylene, polyester, polytetrafluorethylene (PTFE), polyurethane, polycarbonate urethane, polyamide, nylon, polyaryletherketone materials (PAEK), polysulfone, carbon, ceramic, metal, or any other acceptable non-bioresorbable biomaterial fiber. Representative resorbable materials include but are not limited to polyglycolic acid (PGA), polylactic acid (PLA), polycaprolactone (PCL), collagen, silk, chitin, chitosan, hyaluronic acid, or any other acceptable bioresorbable biomaterial fiber.

In a further aspect of the disclosure, the interfacial implant may also be used to deliver cells (e.g., chondrocytes, fibroblasts, progenitor cells, stem cells, reprogrammed cells) and/or additional, exogenously introduced biologically active molecules, such as growth factors, cytokines, chemokines, antibiotics, DNA, plasmids, or other molecules that may induce directed growth and/or differentiation of cells, or vectors capable of delivering bioactive therapeutic genes to the product. The interfacial implant may be at least partially coated with inorganic matrix coatings known to promote bone formation such as, hydroxyapatite, calcium phosphate, calcium carbonate, alumina, zirconia, yttria-stabilized zirconia, silicon nitride-based materials, bioactive glass, and/or glass ceramics. The interfacial implant may also be at least partially coated with extracellular-derived biomaterials such as a cartilage-derived matrix, demineralized bone matrix or other decellularized tissues. In yet another aspect, the interfacial implant may be partially (e.g., on the cartilage layer side) or completely filled with a biomaterial gel consisting of collagen, hyaluronic acid, alginate, agarose, chitosan, gelatin, laminin, fibronectin, interpenetrating networks (networks that are completely biological, all synthetic, or a combination of the two), or fibrin.

Further still, the fibers of the implant according to the present disclosure may be coated with bioactive coatings, for example adeno-associated virus (AAV), lentivirus (LV), naked DNA, peptides, self-assembling peptides, anti-inflammatory drugs, cytokines, cytokines inhibitors, macromolecules native to bone and cartilage (e.g., proteoglycan, cartilage oligomeric matrix protein, hyaluronic acid, collagen type I, collagen type II, and bone morphogenetic proteins) or a combination thereof. A portion of the fibers may be coated with one or more biological agents, and portions may be left uncoated or coated with altogether different agents. One of the benefits of the architecture of the warp interlock fabrics is the ability to coat individual fiber bundles to induce site-specific differentiation of cells on the scaffold.

Referring first to FIG. 1, a two-dimensional (2D) side (sagittal) view of a long bone shows cartilage 1 and bone 2 with an osteochondral defect 3. As illustrated, the defect encompasses both cartilage and bone tissue. Now referring to FIGS. 2-3, the irregular osteochondral defect is precisely prepared to provide a complementary pocket 4 for an interfacial implant 5 constructed as described above. The interfacial implant consolidates the de novo synthesized cartilage tissue 6 and bone 7 as shown in FIG. 4. In a further aspect of the methods of the present disclosure, the interfacial implant 5 is sized in relation to the prepared hole so that an approximate mid-line 5a of the implant is located at the anatomical plane 1-2 where the cartilage meets the bone in native, healthy tissue. With this configuration, the scaffold provided by the implant 5 acts as a common anchor point for the two tissues as well as a site for ingrowth from each of the tissues. It can be appreciated that the preparation of the bone bed within the pocket 4 produces bleeding bone at the base of the pocket. This bleeding bone will quickly infiltrate the lower half of the implant scaffold below the implant mid-line 5a. Tissue ingrowth from the cartilage tissue 6, on the other hand, does not happen immediately but rather occurs over time. However, the implant 5 retains its form and strength as the cartilaginous tissue grows into the implant scaffold.

Figure 6:
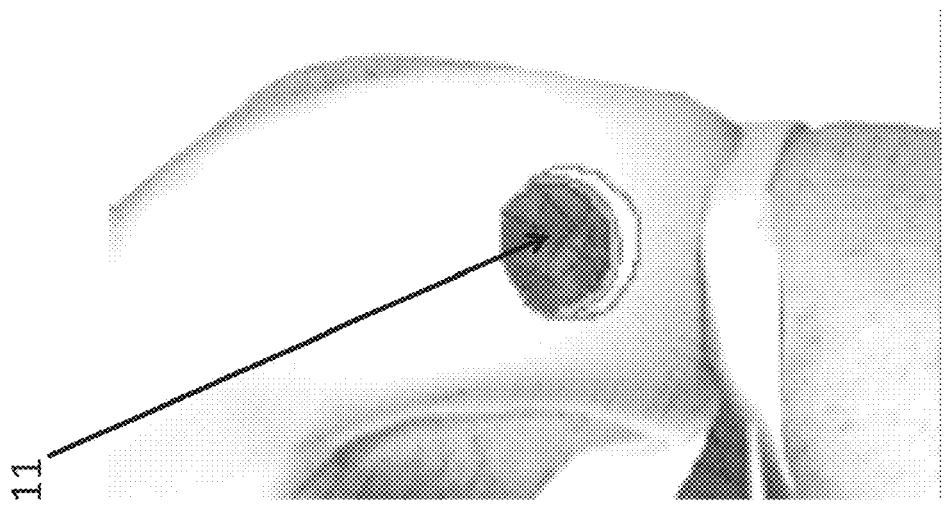
FIG. 6 is a front perspective view of the osteochondral lesion after it has been prepared for the interfacial implant.
Figure 5:
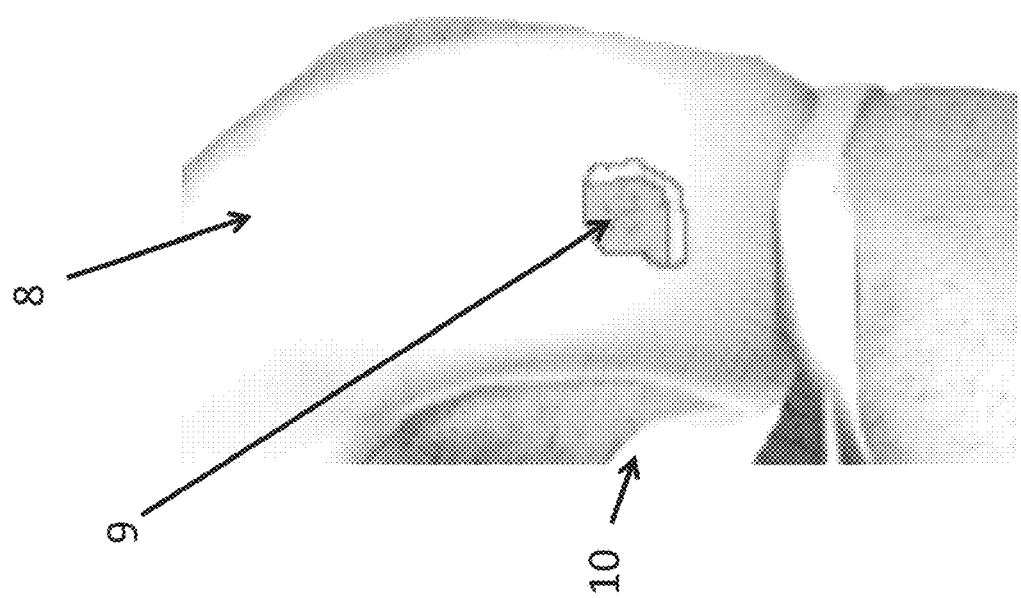
FIG. 5 is a front perspective view of a small osteochondral lesion in the medial femoral condyle of a knee.

Referring now to FIGS. 5-7, the repair of a small osteochondral lesion in the knee and in particular the medial femoral condyle is shown. FIG. 5 depicts a medial femoral condyle 10 with a small osteochondral lesion 9 relative to the size of the condyle. The lesion has penetrated the cartilage 8 and into the underlying bone. In FIG. 6, a reamer, drill, end mill, or other suitable instrument or tool is used to precisely prepare the defect for the interfacial implant. In this example, a hole with a controlled diameter and depth to a flat bottom is prepared. An interfacial implant 12 is prepared as described above to complement the geometry of the prepared hole (FIG. 7).

Figure 10:
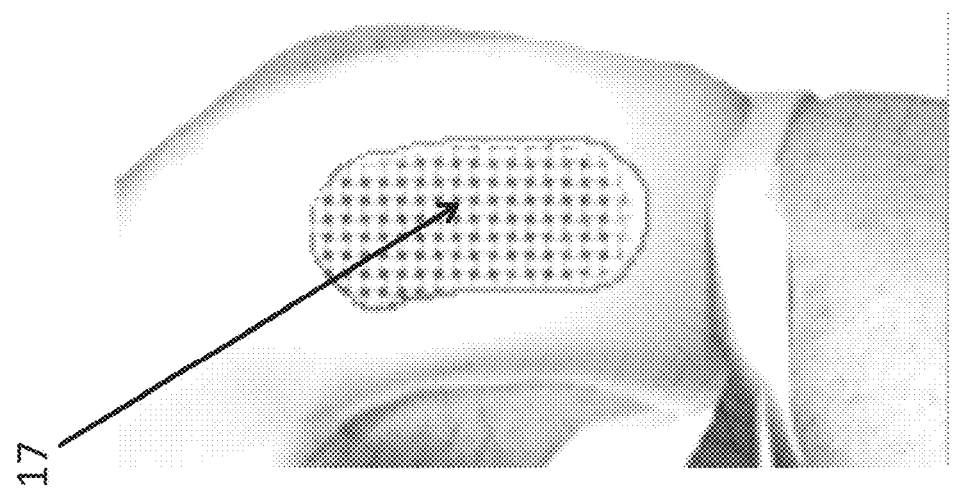
FIG. 10 is a front perspective view after the prepared defect has been filled with the interfacial implant.
Figure 9:
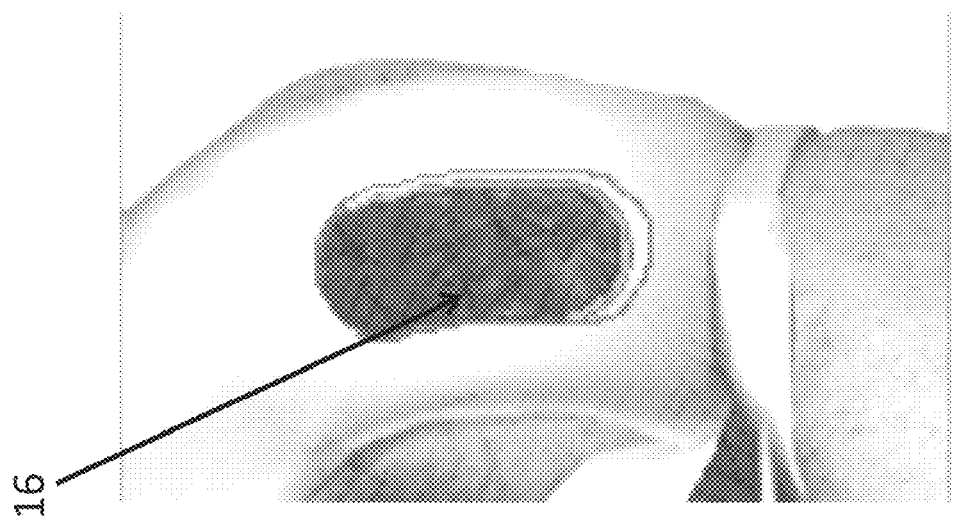
FIG. 9 is a front perspective view of the osteochondral lesion after it has been prepared for the interfacial implant.
Figure 8:
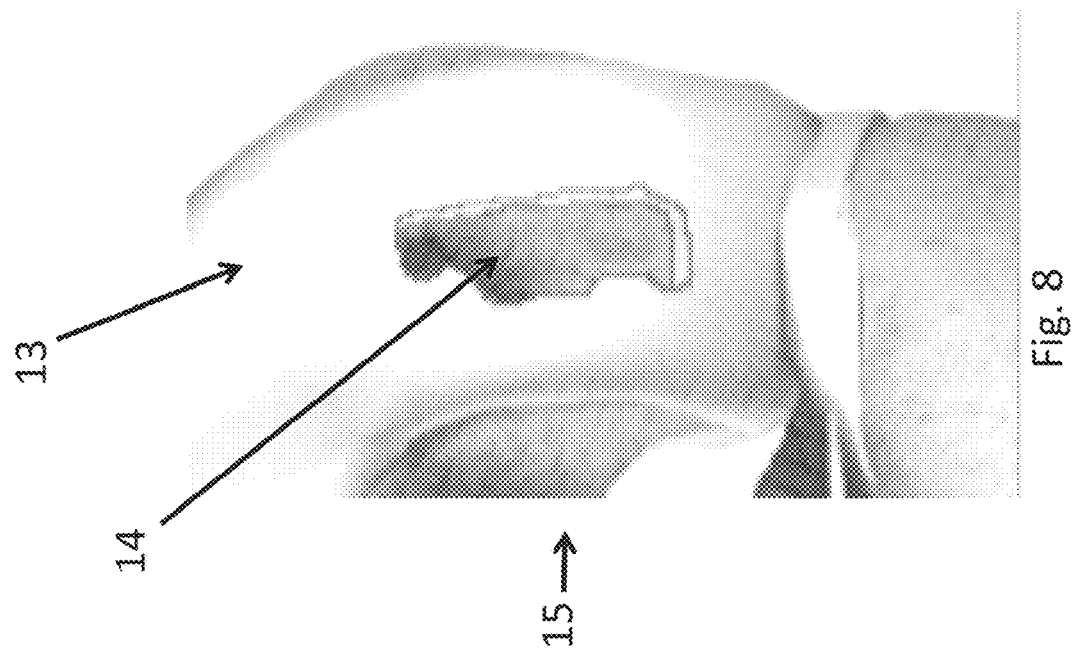
FIG. 8 is a front perspective view of a small osteochondral lesion in the medial femoral condyle of a knee.

FIGS. 8-10 are similar to FIGS. 5-7 but show a large, irregular defect in the condyle in this example. To enable an "off-the-shelf" solution, the geometry of the osteochondral lesion is enlarged to a "standard" shape, in this case a slot or channel 16. The regular channel is formed with the use of surgical instruments such as a drill bit, end mill, burr or other tool that is capable of controllably removing both bone and cartilage. After precise preparation of the footprint of the lesion, an interfacial implant 17 having complementary geometry to the prepared channel 16 is press fit into the defect site.

Figure 11:
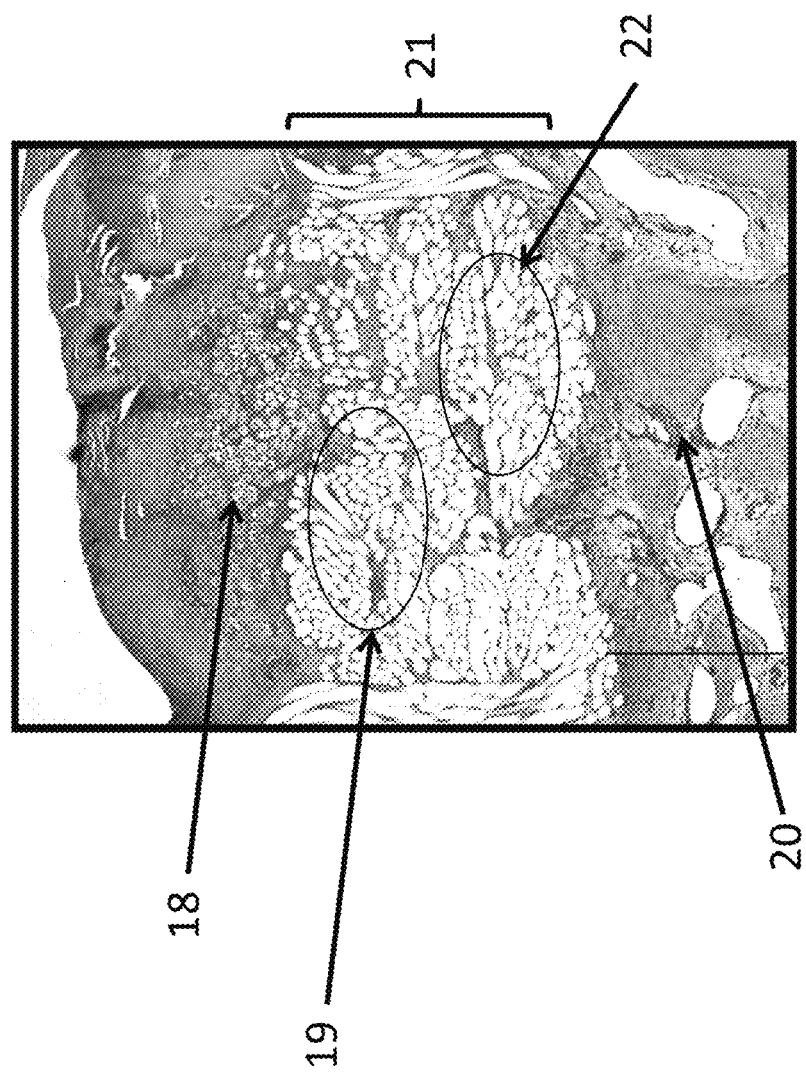
FIG. 11 is a cross-section pathology slide of in vivo data showing the results of an interfacial implant used for repair of an osteochondral defect. The tissues in the image are histologically stained for cartilage and bone.

FIG. 11 is demonstrative of the clinical efficacy of the interfacial implant. An interfacial implant 21 was placed in the osteochondral defect as described, and consolidation of the cartilage and bone tissues is evident in this cross-sectional histology image. Cartilage tissue 19 is found in the upper layers of the interfacial implant as noted by a red Safranin-O stain, and bone tissue is found in the lower layers of the implant, as noted by a bluish-green FastGreen stain in the original histological image. Additionally the interfacial implant shows incorporation with the bone 20 in addition to cartilage tissue 18 forming on the top layers of the interfacial implant 21.

Example 1

A cartilage repair implant is constructed from an orthogonal 3D woven fabric as follows: a biomedical grade yarn (150 µm in diameter) was woven into a 3D orthogonal structure containing eleven in-plane fiber layers; five layers were oriented in the warp (X-direction, or 0° or lengthwise in the loom) direction, six layers were oriented in the weft (Y-direction or 90° to the lengthwise fibers) direction and binding fibers were oriented in the Z-direction. The structure contained twenty-four yarns per centimeter in each of the five warp layers, twenty yarns per centimeter in each of the six weft layers and twenty-four yarns per centimeter in the Z-direction. The interconnected internal pores of the implant has dimensions of 390 µm×320 µm×104 µm, yielding a total void volume of about 70%. After the fabric is woven, the implant is cut to near size, and then molded into the shape of the defect using custom-built molds for the geometry in question. Preferably, the material is stabilized using controlled heating to reorganize the molecular state of the polymers that make up the constituent yarns and lock them into an altered physical conformation. This process, known as "heat setting" stabilizes the structure without sacrificing the porosity in each layer, the through porosity, or the designed mechanical properties of the structure.

Example 2

A cartilage repair implant is constructed from an orthogonal 3D woven fabric as follows: a biomedical grade yarn (150 µm in diameter) was woven into a 3D orthogonal structure containing a total of eleven in-plane fiber layers; five layers were oriented in the warp (0° or lengthwise in the loom) direction, six layers were oriented in the weft (90° to the lengthwise fibers) direction and binding fibers were oriented in the Z-direction. The structure contained twenty-four yarns per centimeter in each of the five warp layers, fifteen yarns per centimeter in each of the six weft layers and twenty-four yarns per centimeter in the Z-direction. The woven yarns formed interconnected internal pores having dimensions of 450 µm×320 µm×104 µm, yielding a total void volume of about 74%. After the fabric is woven, the implant is cut to near size and then molded into the shape of the defect using custom-built molds for the geometry in question. Preferably, the material is stabilized using controlled heating to reorganize the molecular state of the polymers that make up the constituent yarns and lock them into an altered physical conformation. This process, known as "heat setting" stabilizes the structure without sacrificing the porosity in each layer, the through porosity, and the designed mechanical properties of the structure.

Example 3

A cartilage repair implant is constructed from an orthogonal 3D woven fabric as follows: a biomedical grade yarn (150 µm in diameter) was woven into a 3D orthogonal structure eleven in-plane fiber layers; five layers were oriented in the warp (0° or lengthwise in the loom) direction, six layers were oriented in the weft (90° to the lengthwise fibers) direction and binding fibers were oriented in the Z-direction. The structure contained twenty-four yarns per centimeter in each of the five warp layers, twenty yarns per centimeter in each of the six weft layers and twenty-four yarns per centimeter in the Z-direction. Prior to weaving, the top two layers of warp fiber bundles are coated with a lentivirus encoding transforming growth factor—beta (TGF-β) to induce cartilaginous differentiation of cells migrating onto the scaffold after implantation. The bottom three layers of warp fibers are coated with bone morphogenetic factor 2 (BMP-2) to promote osteogenic differentiation of the endogenous stem cells migrating into the scaffold. As in Example 1, the interconnected internal pores had dimensions of 390 µm×320 µm×104 µm, yielding a total void volume of about 70%. After the fabric is woven, the implant is cut to near size, lyophilized, and sterilized using non-heat sterilization methods (e.g., low temperature ethylene oxide sterilization). The implant is removed from packaging at the time of surgery, cut to the shape of the defect and then placed into the defect with the osteogenic side on the prepared bone bed.

Example 4

The cartilage repair implant of Example 1 may be altered to feature different porosities and properties on the two sides of the implant. The porosity of the upper cartilage layer of the structure is reduced by increasing the density of Z-direction binder yarns and decreasing the spacing between the weft yarns through the upper two layers. This has the added benefit of decreasing the roughness of the implant. The pore size in the surface layer (or layers) is effectively decreased to 200 µm×150 µm×50 µm. As in Example 1, the interconnected internal pores in the osteogenic (lower) layers retain dimensions of 390 µm×320 µm×104 µm, yielding a total void volume of about 78%.

The present disclosure should be considered as illustrative and not restrictive in character. It is understood that only certain embodiments have been presented and that all changes, modifications and further applications that come within the spirit of the disclosure are desired to be protected.

REFERENCES

1. Hjelle K, Solheim E, Strand T, Muri R, Brittberg M. Articular cartilage defects in 1,000 knee arthroscopies. Arthroscopy-the Journal of Arthroscopic and Related Surgery. 2002; 18(7):730-4. doi: 10.1053/jars.2002.32839. PubMed PMID: WOS:000177863600009.
2. Buckwalter J A, Martin J A, Brown T D. Perspectives on chondrocyte mechanobiology and osteoarthritis. Biorheology. 2006; 43(3-4):603-9. Epub Aug. 17, 2006. PubMed PMID: 16912432.

3. Praemer A, Furner S, Rice D P. Musculoskeletal Conditions in the United States. Rosemont, Ill.: American Academy of Orthopaedic Surgeons; 1999.
4. Aichroth P M, Patel D V, Moyes S T. A prospective review of arthroscopic debridement for degenerative joint disease of the knee. Int Orthop. 1991; 15(4):351-5. Epub Jan. 1, 1991. PubMed PMID: 1809718.
5. Aubin P P, Cheah H K, Davis A M, Gross A E. Long-term followup of fresh femoral osteochondral allografts for posttraumatic knee defects. Clin Orthop Relat Res. 2001 (391 Suppl):S318-27. Epub Oct. 18, 2001. PubMed PMID: 11603715.
6. Baumgaertner M R, Cannon W D, Jr., Vittori J M, Schmidt E S, Maurer R C. Arthroscopic debridement of the arthritic knee. Clin Orthop Relat Res. 1990 (253):197-202. Epub Apr. 1, 1990. PubMed PMID: 2317974.
7. Denoncourt P M, Patel D, Dimakopoulos P. Arthroscopy update #1. Treatment of osteochondrosis dissecans of the knee by arthroscopic curettage, follow-up study. Orthop Rev. 1986; 15(10):652-7. Epub Oct. 1, 1986. PubMed PMID: 3453907.
8. Emmerson B C, Gortz S, Jamali A A, Chung C, Amiel D, Bugbee W D. Fresh osteochondral allografting in the treatment of osteochondritis dissecans of the femoral condyle. Am J Sports Med. 2007; 35(6):907-14. Epub Mar. 21, 2007. doi: 0363546507299932 [pii] 10.1177/0363546507299932 [doi]. PubMed PMID: 17369560.
9. Friedman M J, Berasi C C, Fox J M, Del Pizzo W, Snyder S J, Ferkel R D. Preliminary results with abrasion arthroplasty in the osteoarthritic knee. Clin Orthop Relat Res. 1984 (182):200-5. Epub Jan. 1, 1984. PubMed PMID: 6692614.
10. Ghazavi M T, Pritzker K P, Davis A M, Gross A E. Fresh osteochondral allografts for post-traumatic osteochondral defects of the knee. J Bone Joint Surg Br. 1997; 79(6):1008-13. Epub Dec. 11, 1997. PubMed PMID: 9393922.
11. Johnson L L. Arthroscopic abrasion arthroplasty: a review. Clin Orthop Relat Res. 2001 (391 Suppl):S306-17. Epub Oct. 18, 2001. PubMed PMID: 11603714.
12. Kish G, Modis L, Hangody L. Osteochondral mosaicplasty for the treatment of focal chondral and osteochondral lesions of the knee and talus in the athlete. Rationale, indications, techniques, and results. Clin Sports Med. 1999; 18(1):45-66, vi. Epub Feb. 24, 1999. PubMed PMID: 10028116.
13. Steadman J R, Briggs K K, Rodrigo J J, Kocher M S, Gill T J, Rodkey W G. Outcomes of microfracture for traumatic chondral defects of the knee: average 11-year follow-up. Arthroscopy. 2003; 19(5):477-84. Epub May 2, 2003. doi: 10.1053/jars.2003.50112. PubMed PMID: 12724676.
14. Steadman J R, Rodkey W G, Rodrigo J J. Microfracture: surgical technique and rehabilitation to treat chondral defects. Clin Orthop Relat Res. 2001 (391 Suppl):S362-9. Epub Oct. 18, 2001. PubMed PMID: 11603719.
15. Wouters E, Bassett F H, 3rd, Hardaker W T, Jr., Garrett W E, Jr. An algorithm for arthroscopy in the over-50 age group. Am J Sports Med. 1992; 20(2):141-5. Epub Mar. 11, 1992. PubMed PMID: 1558240.
16. Nehrer S, Spector M, Minas T. Histologic analysis of tissue after failed cartilage repair procedures. Clin Orthop Relat Res. 1999 (365):149-62. Epub Jan. 11, 2000. PubMed PMID: 10627699.
17. Shapiro F, Koide S, Glimcher M J. Cell Origin And Differentiation In The Repair Of Full-Thickness Defects Of Articular-Cartilage. Journal Of Bone And Joint Surgery-American Volume. 1993; 75A(4):532-53. PubMed PMID: ISI:A1993KZ59000009.
18. Tew S R, Kwan A P, Hann A, Thomson B M, Archer C W. The reactions of articular cartilage to experimental wounding: role of apoptosis. Arthritis Rheum. 2000; 43(1):215-25. Epub Jan. 22, 2000. doi: 10.1002/1529-0131(200001)43:1<215::AID-ANR26>3.0.CO;2-X [doi]. PubMed PMID: 10643718.
19. McNickle A G, Provencher M T, Cole B J. Overview of existing cartilage repair technology. Sports Medicine and Arthroscopy Review. 2008; 16(4):196-201.
20. Nettles D L, Vail T P, Morgan M T, Grinstaff M W, Setton L A. Photocrosslinkable hyaluronan as a scaffold for articular cartilage repair. Ann Biomed Eng. 2004; 32(3):391-7. Epub Apr. 21, 2004. PubMed PMID: 15095813.
21. Chen W C, Yao C L, Wei Y H, Chu I M. Evaluating osteochondral defect repair potential of autologous rabbit bone marrow cells on type II collagen scaffold. Cytotechnology. 2011; 63(1):13-23. Epub Oct. 26, 2010. doi: 10.1007/s10616-010-9314-9. PubMed PMID: 20972620; PMCID: 3021150.
22. Farr J, Cole B, Dhawan A, Kercher J, Sherman S. Clinical cartilage restoration: evolution and overview. Clin Orthop Relat Res. 2011; 469(10):2696-705. Epub Jan. 18, 2011. doi: 10.1007/s11999-010-1764-z [doi]. PubMed PMID: 21240578.
23. Tetteh E S, Bajaj S, Ghodadra N S. Basic science and surgical treatment options for articular cartilage injuries of the knee. J Orthop Sports Phys Ther. 2012; 42(3):243-53. Epub Mar. 3, 2012. doi: 10.2519/jospt.2012.3673. PubMed PMID: 22383075.
24. Bedi A, Feeley B T, Williams R J, 3rd. Management of articular cartilage defects of the knee. J Bone Joint Surg Am. 2010; 92(4):994-1009. Epub Apr. 3, 2010. doi: 10.2106/JBJS.I.00895. PubMed PMID: 20360528.
25. Kalson N S, Gikas P D, Briggs T W. Current strategies for knee cartilage repair. Int J Clin Pract. 2010; 64(10):1444-52. Epub Aug. 19, 2010. doi: 10.1111/j.1742-1241.2010.02420.x. PubMed PMID: 20716151.
26. Patrascu J M, Freymann U, Kaps C, Poenaru D V. Repair of a post-traumatic cartilage defect with a cell-free polymer-based cartilage implant: a follow-up at two years by MRI and histological review. J Bone Joint Surg Br. 2010; 92(8):1160-3. Epub Aug. 3, 2010. doi: 10.1302/0301-620X.92B8.24341. PubMed PMID: 20675765.
27. Siclari A, Mascaro G, Gentili C, Cancedda R, Boux E. A cell-free scaffold-based cartilage repair provides improved function hyaline-like repair at one year. Clinical orthopaedics and related research. 2012; 470(3):910-9. Epub Oct. 4, 2011. doi: 10.1007/s11999-011-2107-4. PubMed PMID: 21965060; PMCID: 3270167.
28. Zantop T, Petersen W. Arthroscopic implantation of a matrix to cover large chondral defect during microfracture. Arthroscopy. 2009; 25(11):1354-60. Epub Nov. 10, 2009. doi: 10.1016/j.arthro.2009.04.077. PubMed PMID: 19896059.
29. Gille J, Schuseil E, Wimmer J, Gellissen J, Schulz A P, Behrens P. Mid-term results of Autologous Matrix-Induced Chondrogenesis for treatment of focal cartilage defects in the knee. Knee Surg Sports Traumatol Arthrosc. 2010; 18(11):1456-64. Epub Feb. 4, 2010. doi: 10.1007/s00167-010-1042-3. PubMed PMID: 20127072.

What is claimed is:

1. An osteochondral interface repair implant for implantation within an osteochondral lesion, comprising:
a moldable biocompatible three-dimensional woven fiber scaffold constructed of a plurality of layers of woven fibers adapted to allow integration of tissue from the cartilage surface and bone surface upon implantation, the plurality of layers of woven fibers including:
  at least one first layer made of fibers oriented in an x-direction;
  at least one second layer made of fibers oriented in a y-direction, the y-direction orthogonal to the x-direction; and
  at least one fiber oriented in a z-direction, the z-direction orthogonal to both the x-direction and the y-direction,
wherein the at least one first layer and the at least one second layer are connected to one another by the at least one fiber oriented in the z-direction,
wherein at least a portion of the fibers are coated with an inorganic matrix from the group consisting of hydroxyapatite, calcium phosphate, calcium carbonate, alumina, zirconia, yttria-stabilized zirconia, silicon nitride-based materials, bioactive glass, and/or glass ceramics,
wherein each of the fibers comprises a plurality of yarns, and the yarns of all of the fibers of the three-dimensional fiber scaffold are configured to be locked into a physical conformation with respect to one another after being molded such that the scaffold is structurally stable, and
wherein the plurality of layers includes an upper cartilage layer including a first plurality of said plurality of layers defining a first pore size and a lower osteogenic layer including a second plurality of said plurality of layers defining a second pore size that is greater than said first pore size.

2. The osteochondral interface repair implant of claim 1, wherein the first plurality of layers of woven fibers are configured to define a void volume of about 70%.

3. The osteochondral interface repair implant of claim 1, wherein:
  the plurality of layers of woven fibers include five of said first layer and six of said second layer.

4. The osteochondral interface repair implant of claim 3, wherein:
  each of the first layers includes twenty-four yarns per centimeter,
  each of the second layers includes fifteen to twenty yarns per centimeter, and
  the at least one fiber oriented in the z-direction includes twenty-four yarns per centimeter.

5. The osteochondral interface repair implant of claim 1, wherein the fibers comprise a monofilament fiber, a multifilament fiber, a hollow fiber, a fiber having a variable cross-section along its length, or a combination thereof.

6. The osteochondral interface repair implant of claim 1, wherein at least a portion of the fibers are coated with one or more biological agents, wherein the one or more biological agents are selected from the group consisting of collagen, hyaluronic acid, alginate, agarose, chitosan, gelatin, laminin, fibronectin, fibrin, proteoglycan, cartilage oligomeric matrix protein, hyaluronic acid, collagen type I, collagen type II, peptide sequences, self-assembling peptides, anti-inflammatory drugs, bone morphogenetic proteins and other cytokines, cytokines inhibitors, cartilage-derived matrix, demineralized bone matrix and/or other decellularized extracellular matrix-derived tissues.

7. The osteochondral interface repair implant of claim 1, wherein at least a portion of the scaffold is partially or completely filled with a biomaterial gel from the group consisting of collagen, hyaluronic acid, alginate, agarose, chitosan, gelatin, laminin, fibronectin, interpenetrating networks containing fully biologic materials, fully synthetic, or mixtures thereof and/or fibrin or combinations thereof.

8. The osteochondral interface repair implant of claim 1, wherein at least a portion of the fibers are coated with virus, plasmids or DNA adapted to transfect or transduce cells within the structure for cartilage and/or bone induction.

9. The osteochondral interface repair implant of claim 1, further comprising one or more cells embedded within the biocompatible three dimensional fiber scaffolds.

10. The joint resurfacing implant of claim 9, wherein the one or more cells are selected from the group consisting of primary cells, undifferentiated progenitor cells, stem cells, induced pluripotent stem cells and combinations thereof, wherein the undifferentiated progenitor cells or stem cells are selected from the group consisting of stem or progenitor cells derived from adipose tissue, bone marrow, synovium, muscle, bone, cord blood, periosteum, and combinations thereof, or wherein the primary cells are selected from the group consisting of chondrocytes, osteoblasts, fibroblasts, fibrochondrocytes, and combinations thereof.

11. The osteochondral interface implant of claim 1, wherein the woven fibers are formed of a biocompatible material selected from the group consisting of an absorbable material, a non-absorbable material, and combinations thereof, wherein the non-absorbable material preferably is selected from the group consisting of a polytetrafluoroethylene (PTFE), an expanded PTFE (ePTFE), a polyamide, a nylon, a polysulfone, a cellulosic, an acrylic, polyvinyl alcohol, carbon, ceramic, a metal, an acrylic, a polycarbonate, a polyester, a polyether, a poly(ether ketone), a poly(ether ether ketone), a poly(ethylene terephthalate), a poly(methyl(meth)acrylate), a polyolefin, a polysulfone, a polyurethane, or wherein the absorbable material preferably is selected from the group consisting of a polyglycolic acid (PGA), a polylactic acid (PLA), a polyglycolide-lactide, a polycaprolactone, a polydioxanone, a polyoxalate, a polyanhydride, a poly(phosphoester), catgut suture, collagen, silk, alginate, agarose, chitin, chitosan, hydroxyapatite, bioabsorbable calcium phosphate, hyaluronic acid, elastin, a polyorthoester, a poly(amino acid), a pluronic/F-12, a poly(ethylene oxide)/poly(ethylene glycol) (PEO/PEG), collagen, gelatin, fibrin, hyaluronic acid, a proteoglycan, elastin, and combinations thereof.

12. The osteochondral interface repair implant of claim 1, wherein the plurality of layers of woven fibers are formed by yarns and/or monofilament having diameter in the range of 25 μm and 300 μm.

13. The osteochondral interface repair implant of claim 12, wherein the plurality of layers of woven fibers are formed by yarns and/or monofilament having diameter in the range of 50 μm and 200 μm.

14. The osteochondral interface repair implant of claim 1, wherein said first pore size is 200 μm x 150 μm×50 μm and said second pore size is 390 μm×320 μm×104 μm.

15. An osteochondral interface implant for implantation within an osteochondral lesion, comprising:
  a moldable biocompatible three-dimensional woven fiber scaffold constructed of a plurality of layers of woven fibers adapted to allow integration of tissue from the cartilage surface and bone surface upon implantation, the plurality of layers of woven fibers including:
    at least one first layer made of fibers oriented in an x-direction;
    at least one second layer made of fibers oriented in a y-direction, the y-direction orthogonal to the x-direction; and at least one fiber oriented in a z-direction, the z-direction orthogonal to both the x-direction and the y-direction, wherein:

the at least one first layer and the at least one second layer are connected to one another by the at least one fiber oriented in the z-direction, each of the fibers comprises a plurality of yarns, and the yarns of all of the woven fibers of the three-dimensional fiber scaffold are configured to be locked into a physical conformation with respect to one another after the scaffold is molded such that the scaffold is structurally stable, wherein the plurality of layers includes an upper cartilage layer including a first plurality of said plurality of layers defining a first pore size and a lower osteogenic layer including a second plurality of said plurality of layers defining a second pore size that is greater than said first pore size.

16. The osteochondral interface implant of claim 15, wherein:

the yarns are made of polymers, said polymers configured so that when the woven fibers are heated the molecular state of the polymers is reorganized to lock the yarns into the physical conformation with respect to one another.

17. The osteochondral interface implant of claim 16, wherein each of the plurality of layers of woven fibers of the three-dimensional fiber scaffold are configured to have a porosity that is not changed after the woven fibers are heated.

18. The osteochondral interface repair implant of claim 15, wherein said first pore size is 200 µm x 150 µm×50 µm and said second pore size is 390 µm×320 µm×104 µm.

* * * * *